United States Patent [19]

Fuchs et al.

[11] 4,423,066
[45] Dec. 27, 1983

[54] COMBATING ARTHROPODS WITH PERFLUOROBENZYL 2,2-DIMETHYL-3-VINYL-CYCLOPROPANE CARBOXYLATES

[75] Inventors: Rainer Fuchs, Wuppertal; Klaus Naumann, Cologne; Wolfgang Behrenz, Overath; Ingeborg Hammann, Cologne; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 13,660

[22] Filed: Feb. 21, 1979

[30] Foreign Application Priority Data

Mar. 11, 1978 [DE] Fed. Rep. of Germany ....... 2810634

[51] Int. Cl.³ .................. A01N 53/00; A61K 31/215; C07C 69/753
[52] U.S. Cl. ....................... 424/305; 424/43; 424/45; 424/308; 560/8; 560/118; 562/405; 562/500
[58] Field of Search .................. 560/8, 118; 424/305, 424/308

[56] References Cited

U.S. PATENT DOCUMENTS 3,786,052  1/1974  Martel et al. ................. 560/118
4,157,397  6/1979  Engel ........................... 560/8
4,157,447  6/1979  Engel ........................... 560/8
4,160,842  7/1979  Engel ........................... 560/8

FOREIGN PATENT DOCUMENTS 2271196  12/1975  France .

Primary Examiner—Vivian Garner
Attorney, Agent, or Firm—Sprung, Horn, Kramer & Woods

[57] ABSTRACT

A pentafluorobenzyl 2,2-dimethyl-3-vinylcyclopropane carboxylate of the formula

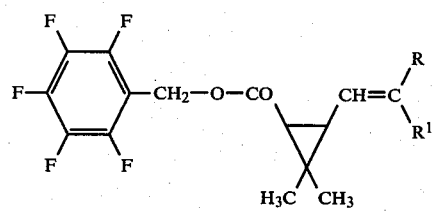

in which
  R is hydrogen or halogen, and
  $R^1$ is optionally substituted phenyl, or
  R and $R^1$ together constitute an alkylene chain with at least two carbon atoms,
which possess arthropodicidal properties.

10 Claims, No Drawings

COMBATING ARTHROPODS WITH PERFLUOROBENZYL 2,2-DIMETHYL-3-VINYL-CYCLOPROPANE CARBOXYLATES

The present invention relates to and has for its objects the provision of particular new perfluorobenzyl 2,2-dimethyl-3-vinyl-cyclopropane carboxylates which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is already known that esters of chrysanthemic acid, for example chrysanthemic acid 2,3,4,5-tetrahydrophthalimido-methyl ester, have insecticidal properties (see Agric. Biol. Chem. 28 (1964), 914).

However, the action of these compounds is not always completely satisfactory, especially when low amounts are used.

The present invention provides, as new compounds, the pentafluorobenzyloxycarbonyl derivatives of the general formula

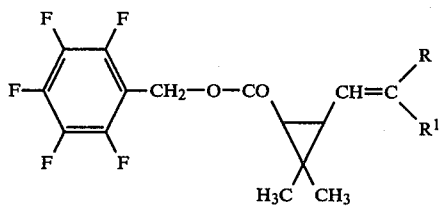

in which

R represents hydrogen or halogen and
$R^1$ represents optionally substituted, phenyl, or
R and $R^1$ together represent an alkylene chain with at least two carbon atoms.

The general formula (I) includes the various possible stereoisomers, the optical isomers and mixtures of these components.

Preferably, R represents hydrogen, chlorine or bromine and $R^1$ represents phenyl, halogenophenyl (especially chlorophenyl or fluorophenyl) or alkylphenyl, the alkyl radical of which contains 1 to 6 (especially 1 to 4) carbon atoms, or R and $R^1$ together represent dimethylene, trimethylene, tetramethylene, pentamethylene or hexamethylene.

Surprisingly, the pentafluorobenzyloxycarbonyl derivatives according to the invention exhibit a better insecticidal and acaricidal action than the corresponding previously known products of analogous structure and the same type of action. The products according to the present invention thus represent a true enrichment of the art.

The invention also provides a process for the production of a pentafluorobenzyloxycarbonyl derivative of the formula (I) in which a carboxylic acid of the general formula

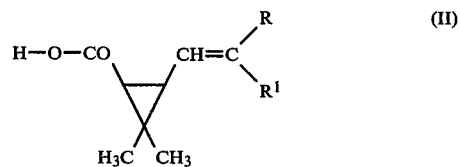

in which

R and $R^1$ have the meanings stated above, or a salt (especially an alkali metal salt) thereof is reacted with a pentafluorobenzyl halide, if appropriate in the presence of an acid acceptor and if appropriate in the presence of an inert solvent or diluent.

If, for example, the sodium salt of 2,2-dimethyl-3-cyclopropylidenemethyl-cyclopropanecarboxylic acid and pentafluorobenzyl bromide are used as starting compounds, the course of the reaction can be represented by the following equation:

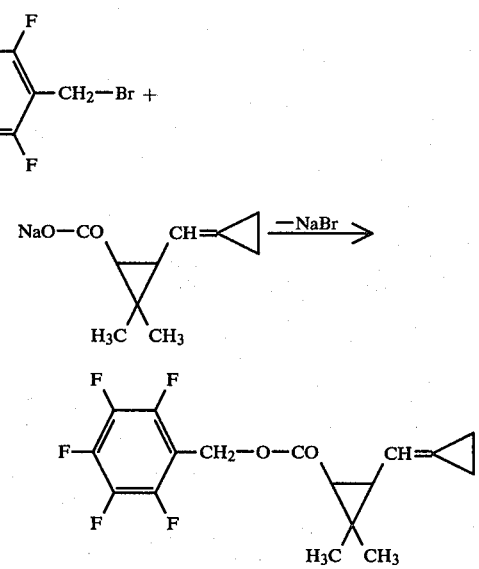

Some of the Compounds of the formula (II) and their salts are known, and they can all be prepared by processes which are known from the literature (see Tetrahedron Lett. 1976, page 4359–4362 or French Patent Specification 2,067,854). The ethyl esters, some of which are known, can be prepared by processes which are known from the literature, for example from 3-formyl-2,2-dimethyl-cyclopropanecarboxylic acid ethyl ester and O,O-dimethylmethanephosphonic acid diester derivatives according to the equation which follows:

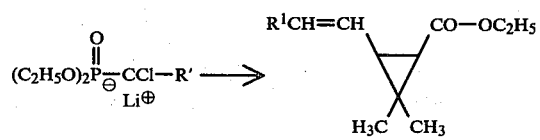

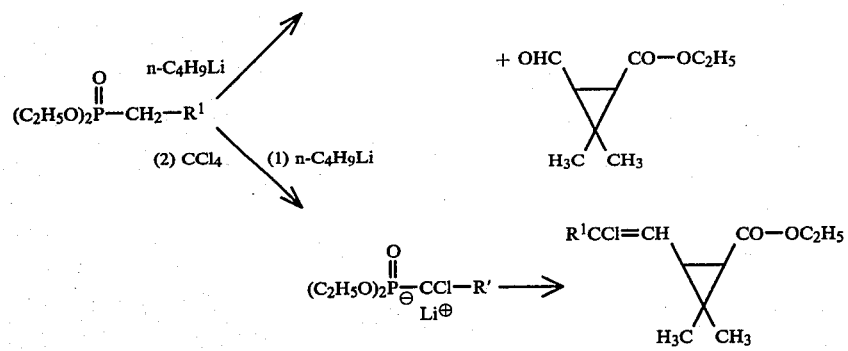

Specific examples which may be mentioned of the cyclopropanecarboxylic acids of the formula (II), or salts thereof, are: 3-(2-phenyl-vinyl)-, 3-(2-(3-chlorophenyl)-vinyl)-, 3-(2-(4-chlorophenyl)-vinyl)-, 3-(2-(3,4-dichlorophenyl-vinyl)-, 2-(2-(4-fluorophenyl)-vinyl)-, 3-(2-(4-methylphenyl)-vinyl)-, 3-(2-(4-ethylphenyl)-vinyl)-, 3-(2-(4-n-propylphenyl)-vinyl)- and 3-(2-(4-isopropylphenyl)-vinyl)-2,2-dimethyl-cyclopropanecarboxylic acid and the sodium or potassium salts thereof, furthermore 3-(2-phenyl-2-chloro-vinyl)-, 3-(2-(3-chlorophenyl)-2-chloro-vinyl)-, 3-(2-(4-chlorophenyl)-2-chloro-vinyl)-, 3-(2-(3,4-dichlorophenyl)-2-chloro-vinyl)-, 3-(2-(4-fluorophenyl)-2-chlorovinyl)-, 3-(2-(4-methylphenyl-2-chloro-vinyl)-, 3-(2-(4-ethylphenyl)-2-chloro-vinyl)-, 3-(2-(4-n-propylphenyl)-2-chloro-vinyl)- and 3-(2-(4-isopropylphenyl)-2-chloro-vinyl)-2,2-dimethyl-cyclopropanecarboxylic acid and the sodium or potassium salts thereof, furthermore 3-(2-phenyl-2-bromo-vinyl)-, 3-(2-(3-chlorophenyl)-2-bromo-vinyl)-, 3-(2-(4-chlorophenyl)-2-bromovinyl)-, 3-(2-(3,4-dichlorophenyl)-2-bromo-vinyl)-, 3-(2-(4-fluorophenyl)-2-bromo-vinyl)-, 3-(2-(4-methylphenyl)-2-bromovinyl)-, 3-(2-(4-ethylphenyl)-2-bromovinyl)-, 3-(2-(4-n-propylphenyl)-2-bromo-vinyl)- and 3-(2-(4-isopropylphenyl)-2-bromo-vinyl)-2,2-dimethylcyclopropanecarboxylic acid and the sodium or potassium salts thereof, and furthermore 3-cyclopropylidenemethyl-, 3-cyclobutylidenemethyl-, 3-cyclopentylidenemethyl-, 3-cyclohexylidenemethyl- and 3-cycloheptylidenemethyl-2,2-dimethylcyclopropanecarboxylic acid and the sodium or potassium salts thereof.

Pentafluorobenzyl bromide, also used as a starting material, is known and can be prepared by reacting pentafluorobenzyl alcohol with hydrobromic acid (J. Chem. Soc. 1961, 808–817).

The process for the preparation of the compounds according to the invention is preferably carried out using a suitable solvent or diluent. Possible solvents or diluents are virtually all the inert organic solvents, especially aprotic dipolar solvents, for example acetone, methyl ethyl ketone, methyl isopropyl ketone and methyl isobutyl ketone, acetonitrile and propionitrile, nitromethane, dimethylformamide and dimethylacetamide, dimethylsulphoxide, tetramethylene sulphone, N-methylpyrrolidone and hexamethylphosphoric acid triamide.

The reaction temperature can be varied within a relatively wide range. In general, the reaction is carried out at from 20° to 200° C., preferably at from 50° to 150° C.

In general, the reaction is allowed to proceed under normal pressure.

For carrying out the process according to the invention, between 0.4 and 1.5 moles of pentafluorobenzyl halide, or the derivative thereof, are employed per mole of the cyclopropanecarboxylic acid derivative (II). The reactants are usually brought together in one of the solvents indicated and the mixture is usually stirred at elevated temperature for one or more hours. After the reaction has ended, the solvent is distilled off or the reaction mixture is poured into water. The product is in each case extracted with an organic solvent, for example with methylene chloride; the organic phase is then worked up in the customary manner by washing with water, drying and distilling off the solvent.

The new compounds are obtained in the form of oils which, in some cases, cannot be distilled without decomposition but which can be freed from the last volatile constituents by so-called "incipient distillation," that is to say by prolonged heating to moderately elevated temperatures under reduced pressure, and can be purified in this way. They are characterized by the refractive index.

The active compounds are well tolerated by plants, have a favorable level of toxicity to warm-blooded animals, and can be used for combating arthropod pests, especially insects or acarids, which are encountered in agriculture, in forestry, in the protection of stored products and of materials, and in the hygiene field. They are active against normally sensitive and resistant species and against all or some stages of development.

The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differenialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp,;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum pedi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Dibrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order off the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The following examples illustrate preparation of the novel compounds:

EXAMPLE 1

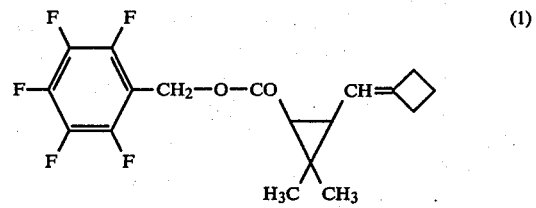

3.6 g (0.0165 mol) of the potassium salt of 2,2-dimethyl-3-cyclobutylidenemethylcyclopropanecarboxylic acid were dissolved in 50 ml of dimethylformamide and the solution was heated to 110° C., together with 4.3 g (0.0165 mol) of pentafluorobenzyl bromide, for 3 hours. After the reaction had ended, the reaction mixture was poured into 150 ml of water and extracted twice with 100 ml of methylene chloride each time. The organic phase was then extracted by shaking twice with 100 ml of water each time and then dried over sodium sulphate. The solvent was stripped off *in vacuo* and last residues of solvent were removed by brief incipient distillation at a bath temperature of 60° C./1 mm Hg. 4.0 g (67.1% of theory) of pentafluorobenzyl 2,2-dimethyl-3-cyclobutylidenemethylcyclopropanecaboxylate were obtained as a brown oil with the refractive index $n_D^{30}$:1.4850.

EXAMPLE 2

(a) The cyclopropanecarboxylic acids, or salts or derivatives thereof, required as starting compounds could be prepared as follows:

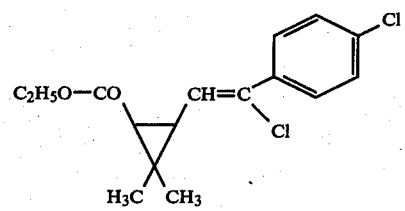

26.3 g (0.1 mol) of 4-chlorobenzyl-phosphonic acid diethyl ester were dissolved in 400 ml of absolute tetrahydrofuran and the solution was cooled to −70° C. 0.11 mol of n-butyl-lithium (15% strength solution in hexane) were added dropwise, in counter-current with nitrogen and while stirring thoroughly, and the reaction mixture was then subsequently stirred at −70° C. for a further 15 minutes. 15.4 g (0.1 mol) of carbon tetrachloride were then added dropwise at −70° C., also under nitrogen, and the reaction mixture thereby became red-brown in color. After stirring for a further 15 minutes, 18.6 g (0.1 mol) of 2,2-dimethyl-3-formyl-cyclopropanecarboxylic acid ethyl ester were added at −65° C. The reaction mixture was then allowed to come to room temperature and was subsequently stirred at 25° C. for a further 3 hours. The reaction mixture was then poured into 2 liters of water and extracted with 600 ml of ether. The ether phase was dried over sodium sulphate, the solvent was stripped off in vacuo and the oily residue was distilled at 150°–155° C./2 mm Hg. 2,2-Dimethyl-3-(2-chloro-2-p-chlorophenyl-vinyl)-cyclopropanecarboxylic acid ethyl ester was obtained in 54.3% yield.

The cyclopropanecarboxylic acid ethyl ester so prepared could be saponified by known methods under acid or alkaline conditions to give the corresponding acid. This could be converted into the corresponding salts (for example alkali metal salts or ammonium salts), by processes which are likewise known.

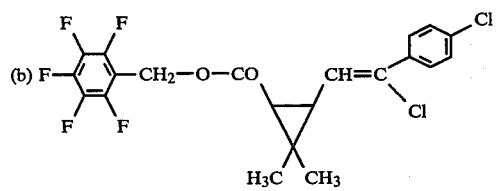

10.7 g (0.033 mol) of the potassium salt of 2,2-dimethyl-3-(2-chloro-2-p-chlorophenyl-vinyl)-cyclopropanecarboxylic acid were dissolved in 100 ml of dimethylformamide and the solution was heated to 120° C., together with 6.8 g (0.026 mol) of pentafluorobenzyl bromide, for 3 hours. After the reaction had ended, the dimethylformamide was distilled off *in vacuo* and the residue which remained was taken up in 200 ml of methylene chloride. The methylene chloride solution was then extracted by shaking twice with 100 ml of water each time, the organic phase was dried over sodium sulphate and the solvent was stripped off in vacuo. Last residues of solvent were removed by brief incipient distillation at a bath temperature of 60° C./1 mm Hg. 9.0 g (74.4% of theory) of pentafluoro-benzyl 2,2-dimethyl-3-(2-chloro-2-p-chloro-phenyl-vinyl)-cyclopropanecarboxylate were obtained as a yellow oil with the refractive index $n_D^{25}$:1.5382.

The compounds which follow could be prepared analogously to either of Examples 1 or 2:

| Compound No. | Formula | |
|---|---|---|
| 3 | 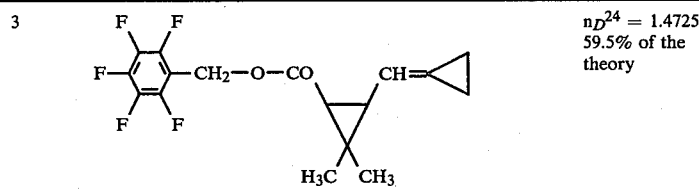 | $n_D^{24} = 1.4725$<br>59.5% of the theory |
| 4 | 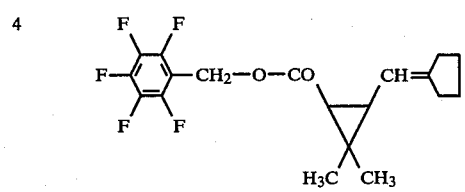 | |
| 5 | 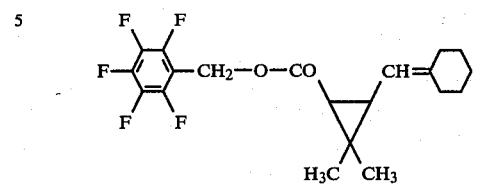 | |
| 6 | 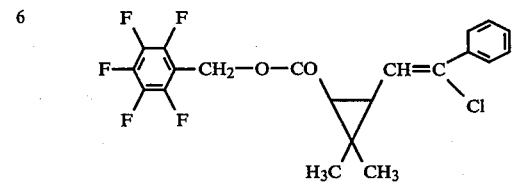 | |
| 7 | 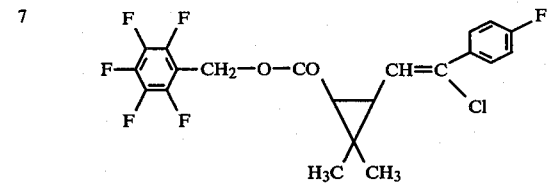 | |

| Compound No. | Formula |
|---|---|
| 8 | 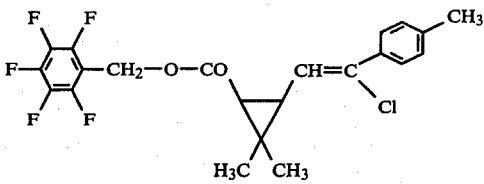 |
| 9 | 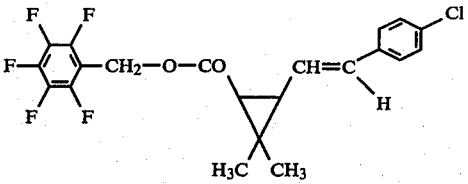 |

The insecticidal and acaricidal activity of the compounds of this invention is illustrated by the following examples wherein the compounds according to the present invention are each identified by the number (given in parentheses) from the preparative examples hereinabove:

EXAMPLE 3

$LD_{100}$ test
Test insects: *Sitophilus granarius*
Number of test insects: 20
Solvent: Acetone The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects were then placed in the Petri dish and it was covered with a glass lid.

The condition of the test insects was observed 3 days after the commencement of the experiments.

In this test, for example, the following compounds showed a superior action compared to the prior art: (1) and (2).

EXAMPLE 4

Mosquito larvae test
Test insects: Aedes aegypti larvae, 4th stage
Solvent: 99 parts by weight of acetone
Emulsifier: 1 part by weight of benzylhydroxydiphenyl polyglycol ether To produce a suitable preparation, the active compound was dissolved, at a rate of 2 g per liter, in the solvent containing the amount of emulsifier stated above. The solution thus obtained was diluted with water to the desired lower concentration.

The aqueous preparations of the active compounds were placed in glass vessels and about 25 mosquito larvae were then placed in each glass vessel.

After 24 hours, the degree of destruction was determined as a percentage. In this test, for example, compound (1) showed a superior action compared to the prior art.

EXAMPLE 5

$LT_{100}$ test for Diptera
Test insects: *Musca domestica* (resistant to P esters and to carbamates)
Number of test insects: 20
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. The stated number of test insects were then placed in the Petri dish and it was covered with a glass lid.

The condition of the test animals was continuously observed along with the time which was necessary for 100% destruction.

In this test, for example, the following compounds showed a superior action compared to the prior art: (1) and (2).

EXAMPLE 6

Laphygma test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Cabbage leaves (*Brassica oleracea*) were treated by being dipped into the preparation of active compound of the desired concentration and were infested with caterpillars of the owlet moth (*Laphygma frugiperda*), as long as the leaves were still moist.

After the specified periods of time, the destruction in % was determined.

In this test, for example, the following compounds showed a superior activity compared to the prior art: (1) and (2).

EXAMPLE 7

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage.

In this test, for example, the following compounds showed a superior activity compared to the prior art: (1) and (2).

EXAMPLE 8

Critical concentration test/soil insects
Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared to the prior art: (1) and (2).

EXAMPLE 9

Test with parasitic adult cattle ticks (*Boophilus microplus* res.)
Solvent: Alkylaryl polyglycol ether To produce a suitable preparation of active compound, the active substance in question was mixed with the stated solvent in the ratio of 1:2 and the concentrate thus obtained was diluted with water to the desired concentration.

10 adult cattle ticks (*B. microplus* res.) were dipped for 1 minute into the active compound preparation to be tested. After transfer into plastic beakers and storage in a climatically controlled chamber, the degree of destruction was determined.

In this test, for example, the following compounds showed a superior action to the prior art: (1) and (2).

It will be appreciated that the instant specification and examples are set forth by way of illustration and not limitation, and that various modifications and changes may be made without departing from the spirit and scope of the present invention.

What is claimed is:

1. A pentafluorobenzyl 2,2-dimethyl-3-vinylcyclopropane carboxylate of the formula

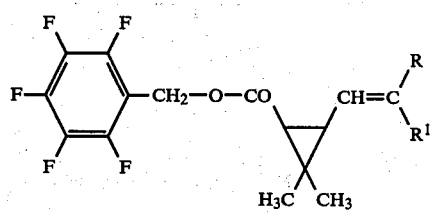

in which
R is hydrogen or halogen, and
$R^1$ is phenyl, halogeno phenyl or $C_{1-6}$-alkyl phenyl, or
R and $R^1$ together constitute an alkylene chain with two to six carbon atoms.

2. A compound according to claim 1, wherein
R is hydrogen, chlorine or bromine, and
$R^1$ is phenyl, halogenophenyl or $C_{1-6}$-alkylphenyl, or
R and $R^1$ together constitute dimethylene, trimethylene, tetramethylene, pentamethylene or hexamethylene.

3. A compound according to claim 1, wherein such compound is pentafluorobenzyl 2,2-dimethyl-3-cyclobutylidenemethyl-cyclopropanecarboxylate of the formula

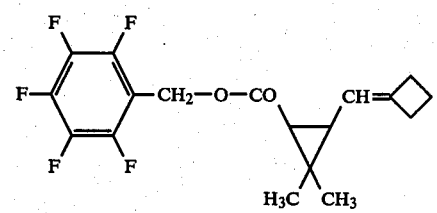

4. A compound according to claim 1, wherein such compound is pentafluorobenzyl 2,2-dimethyl-3-(2-chloro-2-p-chloro-phenyl-vinyl)-cyclopropanecarboxylate of the formula

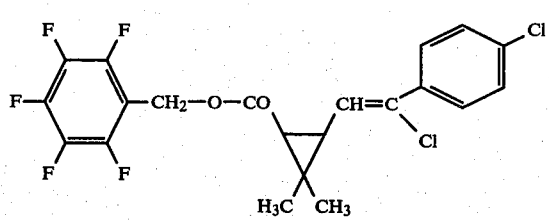

5. A compound according to claim 1, wherein such compound is pentafluorobenzyl 2,2-dimethyl-3-cyclopropylidenemethyl-cyclopropanecarboxylate of the formula

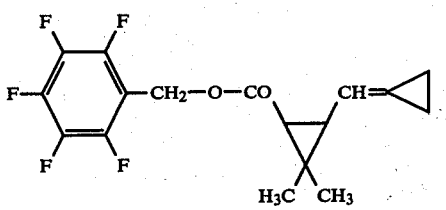

6. A compound according to claim 1, wherein such compound is pentafluorobenzyl 2,2-dimethyl-3-cyclopentylidenemethyl-cyclopropanecarboxylate of the formula

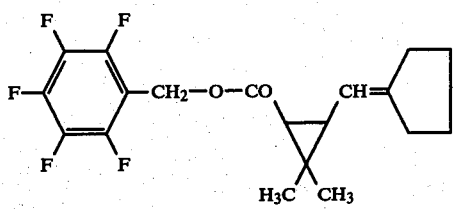

7. A compound according to claim 1, wherein such compound is pentafluorobenzyl 2,2-dimethyl-3-cyclohexylidenemethyl-cyclopropanecarboxylate of the formula

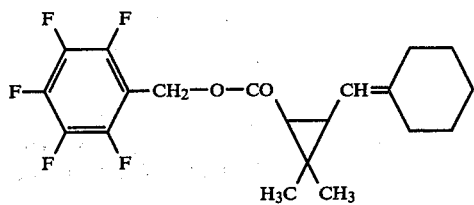

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9, in which there is applied to a domesticated animal pentafluorobenzyl 2,2-dimethyl-3-cyclobutylidenemethyl-cyclopropanecarboxylate, pentafluorobenzyl 2,2-dimethyl-3-(2-chloro-2-p-chloro-phenyl-vinyl)-cyclopropanecarboxylate, pentafluorobenzyl 2,2-dimethyl-3-cyclopropylidenemethyl-cyclopropanecarboxylate, pentafluorobenzyl 2,2-dimethyl-3-cyclopentylidenemethyl-cyclopropanecarboxylate, or pentafluorobenzyl 2,2-dimethyl-3-cyclohexylidenemethyl-cyclopropanecarboxylate.

* * * * *